United States Patent [19]

Odle

[11] Patent Number: 5,206,429
[45] Date of Patent: Apr. 27, 1993

[54] NITRATION REACTIONS WITH ACID ANHYDRIDE PROMOTERS

[75] Inventor: Roy R. Odle, Schuylerville, N.Y.

[73] Assignee: General Electric Company, Pittsfield, Mass.

[21] Appl. No.: 379,665

[22] Filed: Jul. 13, 1989

Related U.S. Application Data

[63] Continuation of Ser. No. 170,708, Mar. 14, 1988, abandoned, which is a continuation of Ser. No. 945,585, Dec. 23, 1986, abandoned, which is a continuation of Ser. No. 567,484, Jan. 3, 1984, abandoned.

[51] Int. Cl.$^5$ .............................................. C07C 205/00
[52] U.S. Cl. .................................... 562/434; 549/243; 562/438
[58] Field of Search ......................... 562/434; 549/243; 560/438

[56] References Cited

U.S. PATENT DOCUMENTS

| | | | |
|---|---|---|---|
| 3,397,229 | 8/1968 | Welch | 562/434 |
| 3,415,876 | 12/1968 | Boonstra et al. | 562/434 |
| 3,681,444 | 8/1972 | Sullivan | 562/434 |
| 4,036,838 | 7/1977 | Vogel et al. | 562/434 |

OTHER PUBLICATIONS

Kampo et al., Chem. Abstr. vol. 79, No. 194832v (1973).

Primary Examiner—Michael L. Shippen

[57] ABSTRACT

An improved all nitric acid nitration process for the nitration of phthalic acid, phthalic anhydrides and derivatives thereof wherein the improvement consists essentially of employing a rate enhancing amount of a nitration promoting inorganic acid anhydride to enhance the rate of nitration.

15 Claims, No Drawings

NITRATION REACTIONS WITH ACID ANHYDRIDE PROMOTERS

This is a continuation of application Ser. No. 170,708, filed Mar. 14, 1988, now abandoned which is a continuation of Ser. No. 945,585, filed Dec. 23, 1986, now abandoned which is a continuation, of application Ser. No. 567,484 filed Jan. 3, 1984, now abandoned.

The present invention relates to an improved process for the nitration of phthalic acids, phthalic anhydrides and derivatives thereof. Specifically, in a nitric acid only nitration process, the rate of nitration of phthalic acids, phthalic anhydrides and derivatives thereof may be greatly enhanced by the addition of one or more inorganic acid anhydrides to the reaction mixture.

BACKGROUND

It is known to nitrate various aromatic compounds including, for example, phthalimides phthalic acids, phthalic anhydrides and derivatives thereof by, treatment with a mixture of concentrated sulfuric acid and nitric acid. Specific teachings of these nitration reactions may be found in Takekoshi, U.S. Pat. No. 3,868,389; Bacha et al, U.S. Pat. No. 4,137,419; and Cook et al, U.S. Pat. Nos. 3,933,852, 3,981,933 and 3,887,588.

Recently, it was discovered that aromatic compounds could be nitrated in a nitration reaction which employed only nitric acid. Specifically, copending patent application Ser. No. 917,926, filed Oct. 10, 1912, assigned to the same assignee as the present invention, discloses the nitration of alkylphthalimides in at least 95% concentrated nitric acid. Related copending patent application Ser. No. 886,172 filed May 22, 1986, also assigned to the same assignee as the present invention discloses the nitration of phthalic acids, phthalic anhydrides and derivatives thereof in a nitric acid only nitration process. Both of these copending patent applications teach the preferred use of high temperatures in order to achieve the best rate of nitration, thus short nitration times. However, even at such high temperatures, for example above 50° C., the time for completion of the nitration, or substantially so, may be three hours or more.

More recently, copending patent application Serial No. 06/567,484 filed Jan. 3, 1984 disclosed that the rate of nitration in the nitric acid only nitration of aromatic substrates could be greatly enhanced by the addition of various acid anhydride nitration promoters to the reaction mixture. Specifically, the application disclosed that various organic and inorganic acid anhydrides were useful as nitration promoters in the nitric acid only nitration of aromatic substrates, particularly N-alkyl phthalimides, phthalic acids and phthalic anhydrides. That application further discloses that particular acid anhydride may be less effective or inoperable for certain aromatic substrates.

It has been now found that certain acid anhydride promoters which are generally effective promoters for the enhancement of the rate of nitration for various aromatic substrates are ineffective for the enhancement of the rate of nitration of phthalic acids, phthalic anhydrides and derivatives thereof, in the nitric acid only nitration process.

It is, therefore an object of the present invention to disclose effective acid anhydride nitration promoters for the nitric acid only nitration of phthalic acids, phthalic anhydrides and derivatives thereof.

SUMMARY

It has now been found that the rate of nitration of phthalic acids, phthalic anhydrides and derivatives thereof may be greatly enhanced by the addition of inorganic acid anhydrides as nitration promoters to the reaction mixture in the nitric acid only nitration process. Especially preferred inorganic acid anhydrides include phosphoric anhydride and sulfur trioxide.

Specifically, the present invention provides for an improved process for the nitric acid only nitration of phthalic acids, phthalic anhydrides, and derivatives thereof comprising (1) forming a solution of the aforementioned substrate in a solvent of at least about 95% concentrated nitric acid and an inorganic acid anhydride selected from the group consisting essentially of sulfur trioxide and phosphoric anhydride, (2) reacting the solution at the temperature of from about $-20°$ C. to about the boiling point of nitric acid, (3) allowing the reaction to run to produce the nitrated derivatives thereof and (4) thereafter recovering the nitrated derivatives as product in any manner known to those skilled in the art, wherein the improvement consists essentially of the aforementioned addition of an inorganic acid anhydride promoter to enhance the rate of nitration.

The amount of inorganic acid anhydride used in the process of the present invention is an effective amount sufficient to enhance the rate of nitration. This will generally be from about 0.5 times to about 5 times the stoichiometric amount based on the substrate.

DETAILED DESCRIPTION

The process of the present invention provides for the nitration of phthalic acids, phthalic anhydrides and derivatives thereof at a greatly enhanced rate in the nitric acid only nitration process. Specifically, the use of rate enhancing nitration promoters in the nitric acid only nitration process provides for greatly enhanced rates of nitration even at lower temperatures, with lower weight ratios of nitric acid to aromatic substrate and with lower concentration nitric acids. As disclosed in the above-identified copending patent applications, the nitric acid only nitration process is one which does not require nor employ sulfuric acid in addition to nitric acid in order to conduct the nitration.

In general the improved nitric acid only nitration process of the present invention comprises (1) forming a solution of the phthalic acid, phthalic anhydride or derivative thereof and an effective amount of a rate enhancing inorganic acid anhydride nitration promoter in a solvent of nitric acid, (2) reacting the mixture within a temperature range of from about $-20°$ C. to the boiling point of nitric acid, (3) allowing the nitration to run to produce the nitrated derivatives and (4) thereafter recovering the nitrated products.

The nitric acids useful for the all nitric acid nitration process should have a concentration of at least about 95% by weight and is preferably within the range of from about 97.5 to about 100% concentration. Nitric acids of lower concentration may be used, however, their use results in processes which are too slow to be cost effective. Nitric acids of such concentration are available commercially or may be prepared by known concentrating methods from more widely available commercial nitric acid of 60 to 67% concentration.

The amount of concentrated nitric acid used should be at least of about the stoichiometric amount necessary to attach one nitro ($NO_2$) group on the aromatic nucleus of the aromatic substrate. Generally, the mole ratio of nitric acid to the aromatic substrate should be from about 1 to about 20, preferably from about 1 to about 12, most preferably from about 1 to about 6. Obviously, lower or higher amounts of nitric acid may be used in the all nitric acid nitration process, however, lower amounts of nitric acid result in poor yields and too slow a reaction rate to be cost effective, whereas higher amounts of nitric acid may result in unnecessary spoiling of concentrated nitric acid and increased costs for such acid and its recycling.

The temperature at which the reaction should run should generally fall within the range of from about −20° C. to the boiling point of nitric acid, preferably from about 20° C. to the boiling point of nitric acid, most preferably from about 30° C. to about 70° C. The actual temperature to be employed is dependent upon the desired rate of reaction and the economics of the nitration. More specifically, the higher the temperature the faster the nitration reaction. However, very high temperatures, around the boiling point of nitric acid, should be avoided to prevent the loss of nitric acid due to both boiling and conversion to nitrous oxides.

Temperature also influences the ratio of the 3- and 4- isomers in the reaction products. With higher temperatures said ratio of the 4- isomer to 3- isomer approaches 1:1 whereas at lower temperatures the ratio approaches about 3:2.

For the purpose of this specification and the appended claims, the "boiling point of nitric acid" is defined as the temperature at which the specific nitric acid used, under the pressure employed, boils. This definition is necessitated by the fact that nitric acids of less than 100% concentration have a higher boiling point than 100% concentrated nitric acid and that the boiling point of nitric acid may be elevated by raising the pressure under which the reaction takes place above atmospheric. Such instances are clearly intended to be within full scope of the present invention as set forth in this specification and claimed by the appended claims.

It should also be noted that temperatures outside the range of temperatures disclosed above may be employed with the present process. However, lower temperatures result in a reaction rate which is too slow to be cost effective, whereas higher temperatures require operation at above atmospheric pressure to prevent boiling and subsequent loss of nitric acid.

Briefly, the pressure range under which this process operates may vary from vacuum to above atmospheric pressure. Depending on the type of reactor or reactors employed, they may preferentially operate under slight vacuum for process and safety reasons. Otherwise, the process is generally run at about atmospheric pressure.

The nitric acid only nitration process is generally applicable to the nitration of aromatic compounds, particularly the phthalimides, phthalic acids, phthalic anhydrides and derivatives thereof. Most preferably, the present invention relates to the improved nitric acid only nitration of phthalic acids, phthalic anhydrides and derivatives thereof.

Phthalic acids and phthalic anhydrides useful in the present invention are well known and widely available commercially. Sources for these materials include Mallinckrodt, Inc. of St. Louis, Mo.; Monsanto Company, of St. Louis, Mo.; and Exxon Chemical of Houston, Tex. Further, it is to be understood that phthalic acid and phthalic anhydride include substituted derivatives thereof wherein the aromatic ring of the acid or anhydride is substituted with one or more alkyl radicals having 1 to 10, preferably 1 to 4 carbon atoms and/or one or more halogen atoms, as well as functional derivatives thereof including the diacids, dianhydrides, acid anhydrides, acid halides and other halo derivatives thereof, for example trimelletic acid, pyromelletic acid, trimelletic acid anhydride, pyromelletic dianhydyride, phthalylchloride and the like.

As taught by the aforementioned copending patent applications, the rate of reaction may be varied based on the weight ratio of reactants, the specific reactants and nitric acid used, and, most importantly, the temperature at which the nitration reaction is conducted. It has now been found that the rate of nitration may be greatly enhanced by adding to the reaction mix an inorganic acid anhydride nitration promoter.

Suitable inorganic acid anhydrides include for example boric anhydride, chromic anhydride, phosphoric anhydride and sulfur trioxide. Especially preferred are the phosphoric anhydride and sulfur trioxide, most preferably the sulfur trioxide. All of these inorganic acid anhydrides are generally known compounds and available commercially.

Generally, the inorganic acid anhydride should be added to the reaction mixture in an effective amount to enhance the rate of nitration. While it is expected that smaller amount will enhance the rate of nitration, it is preferred that the amount of acid anhydride promoters be from about 0.5 times to about 5 times the stoichiometric amount, preferably from about 0.8 times to about 2 times the stoichiometric amount, based on the substrate to be nitrated. Most preferably, the amount of acid anhydride used should be of about the stoichiometric amount.

Of course it is to be understand that the effectiveness of certain acid anhydrides will vary depending upon the particular substrate to be nitrated and in certain limited instances, as disclosed in the present patent application, are inoperable. However, it may be possible to predict the effectiveness of certain acid anhydrides by assessing their effectiveness with a particular substrate and then comparing that substrate's propensity to nitrate with the new substrate to be nitrated. For example, it would be expected that all acid anhydrides that show rate enhancement for e.g. phthalic acid would greatly enhance nitrations of other substrates whose propensity to nitration was equal to or greater than that of phthalic acid.

The mode of mixing and the sequence of addition of reactants is not critical to the operability of the process of the present invention. For example, the acid anhydride promoter may be added to the nitric acid prior to, simultaneous with or following addition of the substrate to be nitrated. Additionally, any or all of the substrates may be premixed and then added to the reactor vessel. Again, whether the premix of any two reactants preceeds the addition of the third reactant is not important. It is also possible that any or all reactants or premixes be maintained at the desired reaction temperature, or any other temperature, prior to mixing or entering the reactor.

It is preferred, however, that the nitric acid or nitric acid substrate premix be cooled, preferably to about 0° C. prior to the addition of the nitration promoter and that such mixing takes place in the reactor vessel due to the high reactivity and, more importantly, to the extremely exothermic nature of such mixing. For example, addition of the promoter to nitric acid at room temperature causes immediate and excessing boiling of the nitric acid and may, especially at higher temperature, result in an explosion.

Generally, the process of the present invention comprises mixing the aromatic compound to be nitrated and the acid anhydride together with the concentrated nitric acid in a reactor or reactors preferably equipped with a stirrer or agitating means and means for heating and cooling the reactor. The reactor(s) may be such as to allow for either batch or continuous processing.

Specific variations in the design of the process systems employable to practice the present invention are known to those skilled in the art. For example, it is possible to use one or more reactors in series or in parallel which operate in the plug flow mode with or without radial mixing and with or without heating or cooling. Alternatively, it is possible to use one or more reactors in series or in parallel which operate in the back mixing mode, again with or without heating or cooling and operating in a batch or continuous mode. Finally, it is also possible to use a combination of reactors with features of both foregoing.

The nitration products prepared by the process of the present invention generally comprise a mixture of the 4- and 3- isomer of nitrophthalic acid and may be recovered from the reaction mix by any of the known methods for recovery of nitrated products. Exemplary of the methods available include: extraction; spray drying; precipitation and drying and the like. Recovered unreacted substrate may be reused and the spoiled or used nitric acid may be recycled by known methods for reuse.

The process of the present invention may be modified by the additional step of elevating the temperature of the reactor during or following nitration for a sufficient period of time to reduce or eliminate by-products, particularly dinitro by-products, formed during the nitration process. While essentially any increase in temperature will increase the destruction of such undesirable by-products, it is preferred that the temperature of the reactor be elevated to at least about 40° C., preferably from about 50° C. to about 60° C. Obviously, nitration reactions run at 50° C. or higher will inherently destroy some of the undesirable by-products, however, increasing the temperature even higher will enhance the destruction of said by-products and result in the production of essentially pure nitrated products.

In order that those skilled in the art may better understand how the present invention may be practiced, the following examples are given by way of illustration and not by way of limitation.

DESCRIPTION OF THE PREFERRED EMBODIMENTS

Generally, all reaction products were analyzed by High Pressure Liquid chromotography (HPLC) wherein 50 μl aliquots of the reaction mix were quenched in 3.8 mls. of 0.96M sodium acetate and 0.05M tetraethylammonium bromide. The samples were analyzed on a Waters μ Bondpak/$C_{18}$ column, using a flow rate of 1.5 ml/min and a 280 nm detector. The mobile phase (aqueous phase) for the phthalic acid/anhydride derivatives consisted of a solution of 0.005M tetraethyl-ammonium bromide, 0.035M acetic acid and 0.07M sodium acetate.

EXPERIMENTAL 1

A series of all nitric acid nitration reactions were run to test and demonstrate the effectiveness of various acid anhydride nitration promoters for enhancing the rate of nitration in the all nitric acid nitration of phthalic acid and phthalic anhydride. The specific acid anhydride promoter as well as the amount of promoter and temperature of the reaction were as set forth in Table 1.

In each of these reactions 15 parts by weight of 99% nitric acid was added to a reactor vessel with stirring means and cooled until the acid began to freeze (about 0° C.). The acid anhydride promoter was then added to the cooled nitric acid and the mixture allowed to reach the desired reaction temperature. Subsequently, 1.5 parts by weight of phthalic acid or phthalic anhydride, as appropriate, was added to the solution and the nitration reaction allowed to run. Table 1 sets forth the results of the evaluation, wherein the effectiveness of the acid anhydride promoter is determined based on the amount of unreacted substrate over time as compared to the control reaction in which no promoter was used.

The results of Table 1 demonstrate clearly the selectivity of certain acid anydride nitration promoters for enhancing the rate of nitration for phthalic acid and phthalic anhydride. Specifically, it is clear that most all inorganic acid anhydrides, specifically the phosphoric anhydride and the sulfur trioxides, particularly the latter, greatly enhanced rate of nitration, whereas the organic acid anhydride promoters, particularly those derived from acetic anhydride, were ineffective and in fact slowed the rate of nitration. It is noted that nitric anhydride, likewise, had a negative effect on the rate of nitration, at least at low temperatures.

Further, comparison of run 3-4 with 8-10, respectively, demonstrates the improvement realized in the rate of nitration by elevating the temperature of the reaction and, more importantly, the synergistic enhancement the combination of both temperature and acid anhydride promoter have on the rate of nitration. Specific comparison of run 4 with run 9 demonstrates the ability to use less promoter at higher temperatures while still retaining exceptional enhancement in the rate of nitration.

Finally, from Table I it is clearly evident that sulfur trioxide is most preferred of the inorganic acid anhydride promoters for rate enhancement of phthalic acids and phthalic anhydrides. Further, because of the extremely high reactivity of the sulfur trioxide, it would be expected that it would enhance nitration of aromatic substrates of even less propensity to nitrate than phthalic anhydride.

TABLE I

| Run | Substrate | Temperature °C. | Acid-Anhydrides Promoter | Amount (pts.) | % Substrate Remaining After Time (M.D.) % Substrate (Min.) | | |
|---|---|---|---|---|---|---|---|
| 1 | Phthalic Anhydride | 30–45 | Control | — | 98.3(10) | | 71.6(120) |
| 2 | Phthalic Anhydride | 30–45 | Nitric Anhydride ($N_2O_5$) | 1.6 | 98.6(10) | | 81.1(120) |
| 3 | Phthalic Anhydride | 40 | Control | — | 97.3(10) | 83.2(60) | 62.4(156) |
| 4 | Phthalic Anhydride | 40 | Phosphoric Anhydride | 1.25 | 88.7(10) | 61.9(60) | 38.8(156) |

TABLE I-continued

| Run | Substrate | Temperature °C. | Acid-Anhydrides Promoter | Amount (pts.) | % Substrate Remaining After Time (M.D.) % Substrate (Min.) | | |
|---|---|---|---|---|---|---|---|
| | | | $P_2O_5$ | | | | |
| 5 | Phthalic Anhydride | 40 | Sulfur Trioxide $SO_3$ | 2.07 | 67.4(10) | 3.96(60) | 0.49(156) |
| 6 | Phthalic Anhydride | 40 | Acetic Anhydride $(CH_3CO)_2O$ | 2.69 | 99.2(10) | 97.7(60) | 96.2(156) |
| 7 | Phthalic Anhydride | 40 | Trifluoroacetic Anhydride $(CF_3CO)_2O$ | 5.56 | 99.3(10) | — | 93.4(156) |
| 8 | Phthalic Anhydride | 70 | Control | — | 92.7(10) | 64.4(10) | 14.1(120) |
| 9 | Phthalic Anhydride | 70 | Phosphoric Anhydride | 0.87 | 82.0(5) | 46.5(30) | 7.70(120) |
| 10 | Phthalic Anhydride | 70 | Sulfur Trioxide | 2.07 | 7.98(5) | 1.96(15) | — |
| 11 | Phthalic Acid | 40 | Control | — | 92.7(10) | 81.2(60) | 63.8(156) |
| 12 | Phthalic Acid | 40 | Sulfur Trioxide | 2.07 | 39.0(10) | 1.14(60) | 0(156) |
| 13 | Phthalic Acid | 40 | Trifluoroacetic Anhydride | 5.56 | 98.5(10) | 96.2(60) | 92.2(156) |

Obviously, other modifications and variations of the present invention are possible in light of the above teachings. It is, therefore, to be understood that changes may be made in the particular embodiments of the invention described which are within the full intended scope of the invention as defined by the appended claims.

I claim:

1. An improved process for the nitration of a phthalic acid substrate, comprising (1) forming a solution of the phthalic acid substrate selected from the group consisting of phthalic acid, phthalic anhydride, halo and $C_1$ to $C_{10}$ alkyl substituted derivatives of either and diacid, dianhydride, acid anhydide and acid halide functional derivatives of the foregoing in a solvent consisting essentially of nitric acid of at least about 95% concentration, (2) reacting the mixture within a temperature range of from about $-20°$ C. to about the boiling point of nitric acid, (3) allowing the nitration reaction to run to produce the nitrated derivatives of the phthalic acid substrate and (4) thereafter recovering the nitrated derivatives by methods known in the art, wherein the improvement consists essentially of adding an effective rate-enhancing amount of a nitration-promoting inorganic acid anhydride to said phthalic acid substrate solution prior to initiation of the nitration reaction as a means of enhancing the rate of nitration.

2. The process of claim 1 wherein the nitration promoting inorganic acid anhydride is selected from the group consisting essentially of phosphoric anhydride and sulfur trioxide.

3. The process of claim 1 wherein the nitration promoting inorganic acid anhydride is sulfur trioxide.

4. The process of claim 1 wherein the nitration promoting inorganic acid anhydride is present in an amount of from about 0.5 times to about 5.0 times the stoichiometric amount based on the amount of substrate.

5. The process of claim 1 wherein the nitration promoting inorganic acid anhydride is present in an amount of from about 0.8 times to about 2 times the stoichiometric amount based on the amount of substrate.

6. The process of claim 1 wherein the nitration promoting inorganic acid anhydride is present in about a stoichiometric amount.

7. The amount of claim 1 wherein the substrate is phthalic acid.

8. The process of claim 1 wherein the substrate is phthalic anhydride.

9. The process of claim 1 wherein the nitric acid is from about 97.5 to about 100% concentrated.

10. The process of claim 1 wherein the mixture is reacted at a temperature of from about 20° C. to the boiling point of nitric acid.

11. The process of claim 1 wherein the mixture is reacted at a temperature of from about 30° C. to about 70° C.

12. The process of claim 1 wherein the mole ratio of nitric acid to substrate is from about 1 to about 20.

13. The process of claim 1 wherein the mole ratio of nitric acid to substrate is from about 1 to 12.

14. The process of claim 1 wherein the mole ratio of nitric acid to substrates is from about 1 to about 6.

15. An improved process for the nitration of phthalic anhydride and halo and $C_1$ to $C_{10}$ alkyl substituted derivatives thereof comprising (1) forming a solution of the phthalic anhydride or derivative thereof in a solvent consisting essentially of at least about 95% nitric acid, (2) reacting the mixture within a temperature range of from about $-20°$ C. to the boiling point of nitric acid, (3) allowing the nitration reaction to run to produce the nitrated derivatives of the phthalic anhydride or derivative thereof and (4) thereafter recovering the nitrated derivatives by methods known in the art, wherein the improvement consists essentially of adding an effective rate-enhancing amount of a nitration-promoting inorganic acid anhydride to said solution of phthalic anhydride or derivative thereof prior to initiation of the nitration reaction as a means of enhancing the rate of nitration.

* * * * *